(12) United States Patent
Higashi et al.

(10) Patent No.: US 9,146,231 B2
(45) Date of Patent: Sep. 29, 2015

(54) METHOD FOR TESTING VASCULAR ENDOTHELIAL DAMAGE AND TESTING KIT

(75) Inventors: Shuji Higashi, Tokyo (JP); Yutaka Nagai, Tokyo (JP); Shotaro Fujii, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 398 days.

(21) Appl. No.: 13/369,962

(22) Filed: Feb. 9, 2012

(65) Prior Publication Data
US 2012/0208293 A1 Aug. 16, 2012

(30) Foreign Application Priority Data
Feb. 14, 2011 (JP) ................................. 2011-029027

(51) Int. Cl.
  G01N 33/50 (2006.01)
  G01N 33/49 (2006.01)
  G01N 33/53 (2006.01)
(52) U.S. Cl.
  CPC ........ G01N 33/5091 (2013.01); G01N 33/5002 (2013.01); G01N 33/491 (2013.01); G01N 33/492 (2013.01); G01N 33/5306 (2013.01); G01N 2800/32 (2013.01)
(58) Field of Classification Search
  CPC .......... G01N 33/5091; G01N 2800/32; G01N 33/5002; G01N 33/491; G01N 33/492; G01N 33/5306
  See application file for complete search history.

(56) References Cited

U.S. PATENT DOCUMENTS

| 2003/0175831 A1 | 9/2003 | Canton et al. |
| 2008/0248488 A1 | 10/2008 | Node et al. |
| 2010/0047335 A1 | 2/2010 | Pedreno Egea et al. |

FOREIGN PATENT DOCUMENTS

| JP | 2003-533698 A | 11/2003 |
| JP | 2008-529702 A | 8/2008 |

(Continued)

OTHER PUBLICATIONS

Nozaki et al. Elevated Plasma Levels of Endothelial Microparticles Add Prognostic Value to Coronary Risk Factors in Patients at High Risk for Coronary Heart Disease (Abstract 6202, Circulation 2008: 118S: 1157).*

(Continued)

*Primary Examiner* — Gail R Gabel
(74) *Attorney, Agent, or Firm* — Fox Rothschild LLP; Peter J. Butch, III; Robert N. Henrie, II

(57) ABSTRACT

An object of the present invention is to provide a method which is capable of carrying out detection and evaluation of the vascular endothelial damage with a high degree of accuracy. According to an aspect of the present invention, there is provided a method for testing vascular endothelial damage with respect to a blood sample collected from living organism comprising the steps of: 1) detecting or determining quantitatively vascular endothelial cell-derived microparticle; and 2) detecting or determining quantitatively tissue factor-containing microparticle. Furthermore, according to another aspect of the present invention, there is provided a testing kit of vascular endothelial damage comprising a first antibody which specifically recognizes the vascular endothelium-derived microparticle, and a second antibody which specifically recognizes the tissue factor-containing microparticle.

9 Claims, 11 Drawing Sheets

(56) References Cited

FOREIGN PATENT DOCUMENTS

| | | |
|---|---|---|
| JP | 2010514433 A | 5/2010 |
| JP | 2010132633 A | 6/2010 |
| WO | 2006087597 A1 | 8/2006 |

OTHER PUBLICATIONS

Trappenburg et al. Elevated numbers and altered subsets of procoagulant microparticles in breast cancer patients using endocrine therapy, Thrombosis Research 127 (4): 363-369 (Jan. 26, 2011).*

Omoto et al. Detection of monocyte-derived microparticles in patients with Type II diabetes mellitus, Diabetologia 45: 550-555 (2002).*

Trappenburg et al., "Elevated numbers and altered subsets of procoagulant microparticles in breast cancer patients using endocrine therapy," (Jan. 26, 2011): vol. 127, No. 4, pp. 363-369.

Gelderman et al., "Flow cytometric analysis of cell membrane micropraticles," Functional Proteomics: Methods and Protocols Humana Press Inc., USA Series: Methods in Molecular Biology (2008), pp. 79-93.

International Search Report issued for European Patent Application No. 12154781.4 on May 25, 2012.

Shet et al., "Sickle blood contains tissue factor-positive microparticles derived from endothelial cells and monocytes," Blood (2003): 102(7):2678-2683.

Office Action issued on Mar. 13, 2013 for EP12154781.4.

Decision of Refusal for Japanese Patent Application No. 2011-029027 issued Sep. 24, 2014.

* cited by examiner

METHOD FOR TESTING VASCULAR ENDOTHELIAL DAMAGE AND TESTING KIT

CROSS-REFERENCE TO RELATED APPLICATIONS

This application claims priority to Japanese Patent Application Number 2011-029027 filed Feb. 14, 2011, the disclosure of which is hereby incorporated by reference in its entirety.

BACKGROUND OF THE INVENTION

1. Field of the Invention

The present invention relates to a novel method for testing vascular endothelial damage and a testing kit.

2. Description of Related Art

Metabolic syndrome is a generic term used to refer to a pathological condition which is a complication of visceral fat obesity and any two or more of hyperglycemia, hypertension and hyperlipemia. This metabolic syndrome is a pathological condition which has to be prevented or improved from the viewpoint of reducing medical cost and securing QOL of aged people for a coming aging society. As for the metabolic syndrome, it has been considered effective to prevent from progress of the symptom by improving a lifestyle.

For the progress of pathogenesis of the metabolic syndrome, it has been acknowledged that the vascular endothelial damage is involved. For example, it has been reported that a population of patients who received damage in the vascular endothelium has a higher incidence of cardiovascular event.

By the way, it is known that activated various cells release vesicle called microparticle (MP; MicroParticle). These microparticles with maximum diameter to 1 or to 2 μm are known as platelet-derived microparticle (PDMP), endothelial cell-derived microparticle (EDMP), monocyte-derived microparticle (MDMP), and the like, depending on derived cell, and are understood that they are playing important role in the living organism.

These MPs contain various kinds of membrane proteins (GpIIb/IIIa, VE-cadherin, and Tissue Factor (TF)), and the like, and are considered to have a role in thrombus formation. In addition, a high MP level in blood circulation has been observed in various pathological conditions. Therefore, it is anticipated that detection and quantitative determination of these MPs may be an important criteria in detection and evaluation of severity of precursor state of thrombosis in the progress of various pathological conditions, and thus, in the evaluation of pathological condition and severity of the metabolic syndrome. And, if preventive medical care based on these evaluations can be realized, usefulness thereof in an aging society which will come from now on is immeasurable.

Conventionally, as to testing techniques of various pathological conditions relevant to the vascular endothelial damage using microparticle as a marker of pathological conditions, for example, JP-A-2003-533698 describes a method for detecting and monitoring the precursor state of thrombosis using platelet-derived microparticle (PDMP) as a marker. In addition, JP-A-2008-529702 describes a method for diagnosing cardiovascular disease, evaluation of prognosis thereof, or evaluation of the presence of progress thereof, similarly using the platelet-derived microparticle (PDMP) as a marker.

Conventionally, as to a method for detection and quantitative determination of the microparticle in a biological sample (for example, in the plasma), for example, a filtration method, an enzyme-linked immunosorbent assay (ELISA) method, and the like have been proposed. However, in the recent years, detection and quantitative determination of MP are widely performed through the use of the flow cytometry method by which size and surface antigen marker of MP can be measured simultaneously. Principle of the flow cytometry method, and the advantage of the method that can identify and determine quantitatively a partial population of cells and cell particles are nowadays well known to the person skilled in the art. And also, in the application other than detection and quantitative determination, the flow cytometry method has already been used, for example, for detection of activated platelet in the blood, and detection of platelet-derived prohemostatic microparticle, and so on. In addition, using the flow cytometry method, multiple measurement objects can be measured simultaneously. Despite this, the method for detection and quantitative determination of MP by the flow cytometry method which has been proposed conventionally is a method for measuring only one type of MP using monochromic fluorescent marker. In this regard, conventional technology has not sufficiently taken advantages of the flow cytometry method.

BRIEF SUMMARY OF THE INVENTION

As mentioned above, using PDMP as an indicator, the technology of performing diagnosis and prognostic assessment of various pathologic conditions has been proposed. However, according to a study conducted by the present inventors, it turned out that the conventionally proposed technique employing only PDMP as an indicator was insufficient to perform determinately detection and evaluation of the vascular endothelial damage. As one of reasons, it was considered that the PDMP level in the plasma would also be elevated by the event other than vascular endothelial damage (for example, by generation of inflammation).

And so, in view of the problem in the conventional technology as mentioned above, an object of the present invention is to provide a method for detecting and evaluating vascular endothelial damage with a higher grade of accuracy.

The present inventors have studied intensively for the purpose of solving the above-described problems. In that process, they tried to examine detection and quantitative determination of various kinds of microparticle in a high-risk patient group of vascular endothelial damage. In addition, they also investigated correlation between respective microparticles. As a result, although not expected at all, it was found that there existed a high correlation between the level of vascular endothelium-derived microparticle (hereinafter, simply referred to as "EDMP") in plasma and the level of microparticle containing tissue factor (TF) (hereinafter, referred to as "tissue factor-containing microparticle" or also as "TF"). On the basis of these findings, it was considered that these two kinds of microparticles might be usable as a marker for pathologic condition, and thus the present invention was completed.

That is, according to the first aspect of the present invention, there is provided a method for testing vascular endothelial damage with respect to a blood sample collected from living organism comprising the steps of;

1) detecting or determining quantitatively vascular endothelial cell-derived microparticle; and 2) detecting or determining quantitatively tissue factor-containing microparticle.

In the above-described test method, it is preferable that step 1) is carried out using a first antibody which specifically recognizes the vascular endothelium-derived microparticle (for example, anti-CD144 serum), and step 2) is carried out using a second antibody which specifically recognizes the tissue factor-containing microparticle (for example, anti-CD142 antibody).

Moreover, in the above-described test method, the first antibody and the second antibody are preferably labeled with a fluorescent dye, and in this case, step 1) and step 2) can be carried out using the flow cytometry method.

Furthermore, for the above-described blood sample, the test method described above preferably further comprises the steps of:

3) detecting or determining quantitatively platelet-derived microparticle; and/or 4) detecting or determining quantitatively monocyte-derived microparticle; and/or 5) detecting or determining quantitatively neutrophil-derived microparticle (NDMP).

In addition, according to another aspect of the present invention, there is provided a method for testing risk-factor relevant to prevention and development of the metabolic syndrome comprising the above-described steps in the above-described method.

In addition, according to still another aspect of the present invention, there is provided a testing kit of vascular endothelial damage comprising:

a first antibody which specifically recognizes the vascular endothelium-derived microparticle, and a second antibody which specifically recognizes the tissue factor-containing microparticle.

In a kit for the above-described test, it is preferable that the first antibody is anti-CD144 antibody, and the second antibody is anti-CD142 antibody.

In addition, in a kit for the above-described test, the first and second antibodies are preferably labeled with a fluorescent dye (for example, fluorescein isothiocyanate, phycoerythrin-Cy5, or phycoerythrin, and the like), and in this case, the above-described testing kit can be used for the test employing the flow cytometry method. Further, in this case, it is preferable that the above-described testing kit further comprises:

first setting beads for defining upper limit position of particle size in the detection area of the vascular endothelium-derived microparticle;

second setting beads for defining upper limit position of particle size in the detection area of the tissue factor-containing microparticle;

beads for calculation with known concentration; and threshold beads for defining threshold value of the minimum intensity in the detection area of the microparticle. It should be noted that a mean particle size of the threshold beads is preferably 0.5 μm; a mean particle size of the beads for calculation is preferably 3 to 7 μm; and a mean particle size of the first and the second setting beads are preferably 1 or 2 μm.

By using the method and the testing kit of the present invention, detection and evaluation of vascular endothelial damage can be performed with a high degree of accuracy. Furthermore, by virtue of performing the detection and evaluation of vascular endothelial damage in this way, eventually the test for the risk-factor relevant to prevention and development of the metabolic syndrome becomes possible. The details of one or more embodiments of the invention are set forth in the description below. Other features, objects, and advantages of the invention will be apparent from the description and from the claims.

DETAILED DESCRIPTION OF THE INVENTION

Figure 1:
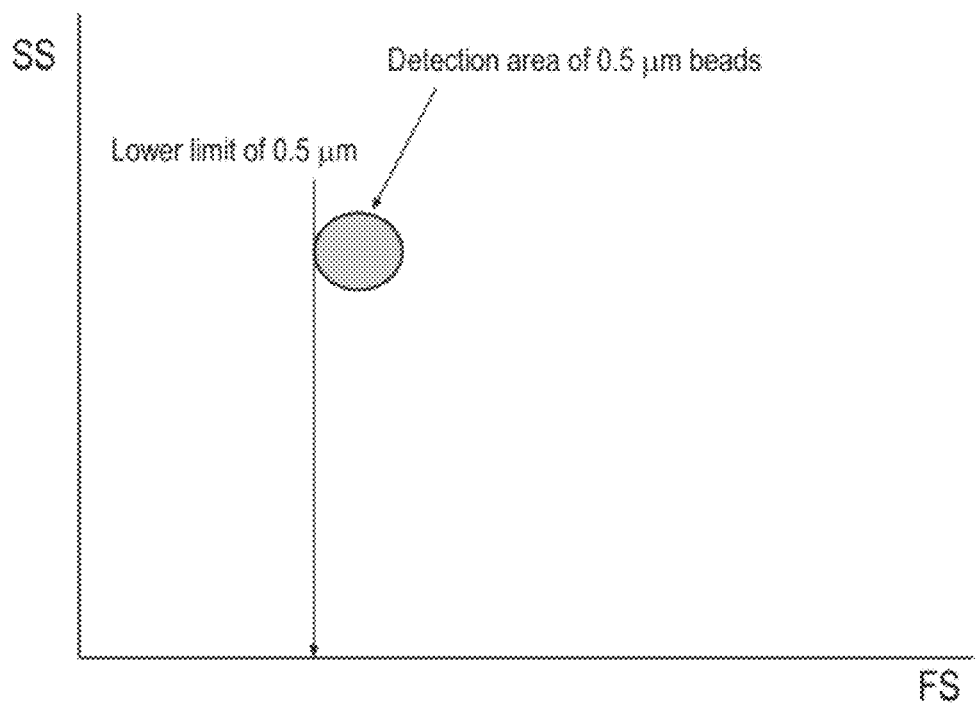
FIG. 1 is an illustrative diagram for explaining a step where a lower limit position of particle size of the MP detection area in FS of FS×SS cytogram is determined by measuring threshold beads which have a mean particle size of 0.5 μm.

The first aspect of the present invention is a method for testing vascular endothelial damage with respect to a blood sample collected from living organism comprising the steps of:

1) detecting or determining quantitatively vascular endothelial cell-derived microparticle (EDMP);

2) detecting or determining quantitatively tissue factor-containing microparticle (TF). Hereinafter, a preferable embodiment for carrying out the test method of the present invention will be explained specifically taking a case where the detection and quantitative determination of MP is performed by the flow cytometry method as an example, however, technical scope of the present invention should be defined based on the description of claims, and should not be limited only to the specific embodiments described below.

In the method of the present invention, the blood sample collected from living organism is used as a sample of the test object. The object which can be applied with the method of the present invention is not particularly limited, as long as it is an animal. The animal includes, for example, mammals. The mammals include, for example, primates, experimental animals, livestock, pets, and the like, and specifically includes, for example, humans, monkeys, rats, mice, rabbits, horses, cattles, goats, sheep, dogs, cats, and the like, although not particularly limited thereto. Preferably, the object animal is human. In addition, the blood sample to be used for the method of the present invention is not particularly limited, and the blood sample commonly used in conventional clinical laboratory test may be used. The blood sample is, for example, plasma sample, and preferably platelet poor plasma (PPP).

Here, in order to detect PDMP which exists at the time of blood collection and to make the PDMP not to be expressed after blood collection, it is important to make platelet not activated. Therefore, in the occasion of preparing blood sample such as plasma sample, it is preferably to use citric acid or EDTA which have Ca ion chelating activity as anticoagulant. In addition, conventionally, the measurement of MP has been performed commonly using a sodium citrate tube, however, in the case where only MP measurement is the object like the method of the present invention, for the purpose of improving sample stability, it is more preferably to use EDTA as anticoagulant.

In addition, since many blood cell components exist in a whole blood sample as compared with MP, in the method of the present invention, it is preferable to use plasma sample rather than whole blood sample as a blood sample. In particular, it is necessary to remove the blood cell components as gently as possible, especially, to avoid contamination of platelet as much as possible, so that excessive MP may not be produced from blood cell in treating process of the whole blood sample. To remove blood cell component from whole blood sample and to obtain plasma sample, plasma component may be separated by centrifugation. In this case, there is no limitation especially on the condition of centrifugation, and can be used in such a condition, for example, at 8000 g for 5 minutes, which is the simplest method. In addition, as a sample container, a microfuge tube made from PP may be used.

Then, after blood cells have been precipitated, supernatant plasma is transferred to another sample container (such as a microtube made from PP) and used as a sample for measurement of the flow cytometry method. The plasma obtained by centrifugation is stored at a temperature, for example, at around 4° C., and used immediately. Alternatively, it is cryopreserved at low temperature of below −20° C. before use, and is used immediately after thawing.

Subsequently, MP in the sample for measurement is subjected to immunostaining. Specifically, antibody is added to the sample for measurement so as to provide antibody concentration required for immunostaining, and reacted with surface antigen of MP contained in the sample. On this occasion, to ensure the satisfied antigen-antibody immunoreaction process, the maximum value of MP concentration in the sample for measurement is estimated, and a sufficient amount of antibody to be added for staining is confirmed in advance. If the antibody concentration is inadequate, another antibody may be trapped in antigen-antibody binding site, and may provide false-positive pattern. The reaction condition for sufficiently promoting the antigen-antibody reaction between antibody and surface antigen is not particularly limited, and conventionally well-known knowledge may be appropriately referred to. For example, it may be performed by incubation at room temperature for about 5 to 30 minutes. In this regard, however, from a view point of protecting fluorescent dye from adverse influence, it is preferable to perform incubation under a shaded condition. In addition, after completion of the reaction, the sample for measurement may be diluted using buffer solution (for example, phosphate buffered saline (PBS) and the like). On this occasion, for the purpose of preventing aggregation of MP, it is preferable to add an aggregation preventing agent such as bovine serum albumin (BSA) by a concentration of about 0.1%.

To perform detection or quantitative determination of vascular endothelial cell-derived microparticle (EDMP) by the flow cytometry method, an antibody, which recognizes EDMP specifically and is labeled with fluorescent dye, is used. As the antibody which recognizes EDMP specifically and corresponds to the surface antigen owned by it, anti-CD144 polyclonal antibodies, anti-CD105 antibody, anti-CD146 antibody, and anti-CD62E antibody and so on, can be used. Among them, anti-CD144 polyclonal antibodies is preferably used. Similarly, to perform detection or quantitative determination of tissue factor-containing microparticle (TF) by the flow cytometry method, an antibody, which recognizes TF specifically and is labeled with fluorescent dye, is used. As the antibody which recognizes TF specifically and corresponds to the surface antigen owned by it, anti-CD142 antibody and the like can be used.

The fluorescent dye to be used for fluorescence labeling of the antibody is not particularly limited, and conventionally well-known knowledge in this field may be appropriately referred to. Said fluorescent dye includes, for example, fluorescein isothiocyanate (FITC), phycoerythrin (PE), PE-Cy5, Cy3, Cy5, Cy5.5, PerCP, PE-Cy5.5, PE-Cy7, PerCP-Cy5.5, and the like. As mentioned above, there is such an advantage by the flow cytometry method that multiple measurement objects can be measured simultaneously. To realize this, respective two or more different antibodies which are desired to be measured simultaneously may be labeled with fluorescent dyes which are different from each other.

In addition, to make the quantitative determination of EDMP and TF in a blood sample by the flow cytometry method possible, the sample for measurement is added with beads for calculation in advance. Specifically, a tube for measurement in which certain amount of beads for calculation has been already contained (for example, TruCount Tube™ (produced by BD Biosciences), or the like) may be used; or else, separately prepared beads for calculation (for example, polystyrene beads (produced by Polyscience, Philadelphia, USA), or the like) may be measured and added in a tube for measurement. Mean particle size of the beads for calculation to be used on this occasion is preferably a larger particle size than platelet, which is different from the particle of measurement object, preferably it is 3 to 7 µm, and more preferably it is 3 µm.

According to the study conducted by the present inventors, with respect to measurement sample derived from patients who are a high risk group of vascular endothelial damage, it was found for the first time that very high correlation was observed between EDMP concentration and TF concentration. The test method of the present invention can perform investigation of vascular endothelial damage based on this finding. Specifically, for example, EDMP concentration and TF concentration in a blood sample collected from test subject are compared with EDMP concentration and TF concentration in a blood sample collected from each healthy subject and patient who was diagnosed definitely as vascular endothelial damage, and thereby it is possible to test for the presence of vascular endothelial damage in the test subject, and the degree of the damage when the vascular endothelial damage is present. In particular, when the values of both EDMP concentration and TF concentration are significantly-high as compared with healthy subject or not significantly-low as compared with the patient who was definitely diagnosed, it can be determined that the possibility of presence of vascular endothelial damage is very high. In addition, specific procedures for measuring EDMP concentration and TF concentration in the blood sample will be described later.

Furthermore, for the above-described blood sample, the method of the present invention preferably further comprises the steps of:

3) detecting or determining quantitatively platelet-derived microparticle (PDMP); and/or 4) detecting or determining quantitatively monocyte-derived microparticle (MDMP); and/or 5) detecting or determining quantitatively neutrophil-derived microparticle (NDMP).

In said aspect, to perform detection or quantitative determination of PDMP, MDMP, and NDMP dose by the flow cytometry method, antibodies which specifically recognize each of them and are labeled with fluorescent dye are used. As the antibody which specifically recognizes PDMP and corresponds to the surface antigen owned by it, anti-CD41 antibody, anti-CD62P antibody, and anti-CD61 antibody and so on, can be used. Among them, anti-CD41 antibody is preferably used. Similarly, to perform detection or quantitative determination of monocyte-derived microparticle (MDMP) by the flow cytometry method, an antibody which specifically recognizes MDMP and is labeled with a fluorescent dye is used. As the antibody which specifically recognizes MDMP and corresponds to the surface antigen owned by it, anti-CD11b (Mac-1) antibody, anti-CD32 antibody, anti-CD33 antibody, and anti-CD14 antibody and so on, can be used. Among them, anti-CD11b (Mac-1) antibody is preferably used. Similarly, to perform detection or quantitative determination of neutrophil-derived microparticle (NDMP) by the flow cytometry method, an antibody which specifically recognizes NDMP and is labeled with a fluorescent dye is used. As the antibody which specifically recognizes NDMP and corresponds to the surface antigen owned by it, anti-CD66b antibody, anti-CD56 antibody, anti-CD16 antibody, and anti-CD64 antibody and so on, can be used. Among them, anti-CD66b antibody is preferably used.

According to the above-described embodiments comprising step 3) and/or step 4) and/or step 5), in addition to the information obtained above on the EDMP concentration and TF concentration in a plasma, the information such as PDMP concentration and/or MDMP concentration can also be utilized in all for the test. Such information is preferable because more elaborate testing (for example, subtyping of pathological condition) becomes possible by said information. Moreover, PDMP concentration in a plasma can be used as an indicator which reflects the state of coagulation system in the blood concerned. Therefore, for example, when the test subject is a patient who is in the onset of hyperlipemia and taking anticoagulant drug, on the basis of the obtained information on the PDMP concentration, clinical efficacy (therapeutic effect and prophylactic effect) of the taking anticoagulant drug can also be tested simultaneously. Furthermore, MDMP is in connection with the case where immunity is inactivated, such as HPS (hemophagocytic syndrome). NDMP is in connection with the case where inflammation is related. In consequence, simultaneous measurement is effective in analysis of the cause of endothelial damage.

In addition, according to another aspect of the present invention, there is also provided a method for testing risk factor related to prevention and development of metabolic syndrome, which comprises the above-described step in the above-described test method.

Specific procedures for detection and quantitative determination of MP such as EDMP and TF by the flow cytometry method are not particularly limited, and conventionally well-known knowledge can be appropriately referred to, as long as the correct value can be obtained accurately. Hereinafter, an example of said procedures will be explained briefly by taking the case where detection and quantitative determination of EDMP and TF is performed simultaneously as an example, and by referring to drawings.

First, prior to the measurement using a measurement sample, TF detection area and EDMP detection area are decided.

Specifically, at first, a FS×SS cytogram is prepared. In this case, in the flow cytometry method, the MP, having a particle size lower than 0.5 μm, cannot be analyzed in principle by a difference in intensity of forward-scattered light (FS). Consequently, here, as shown in FIG. 1, threshold beads having a mean particle size of 0.5 μm are measured, and lower limit position of the particle size of MP detection area in FS is determined.

Figure 2:
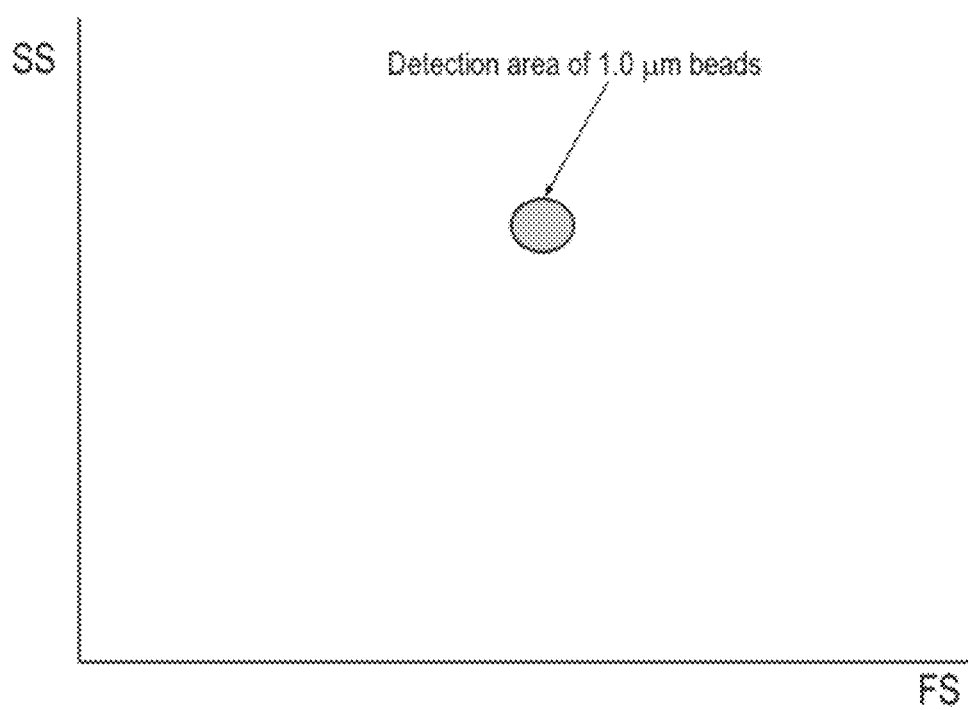
FIG. 2 is an illustrative diagram for explaining a step where an upper limit position of particle size of the TF detection area in FS of FS×SS cytogram is determined by measuring setting beads which have a mean particle size of 1.0 μm.

Subsequently, according to the study conducted by the present inventors, for the TF as well as PDMP and MDMP which may be used optionally, it was concluded that it was appropriate to set the upper limit of particle size to be 1.0 μm. Consequently, here, as shown in FIG. 2, the setting beads having a mean particle size of 1.0 μm are measured, and by a peak value of said setting beads, upper limit position of the particle size of TF detection area in FS is determined.

On the basis of the lower limit position and the upper limit position of particle size of MP detection area which have been set by the procedures mentioned above, as shown in FIG. 3, primary region (primary gate) for TF detection is determined on the FS×SS cytogram.

Figure 4:
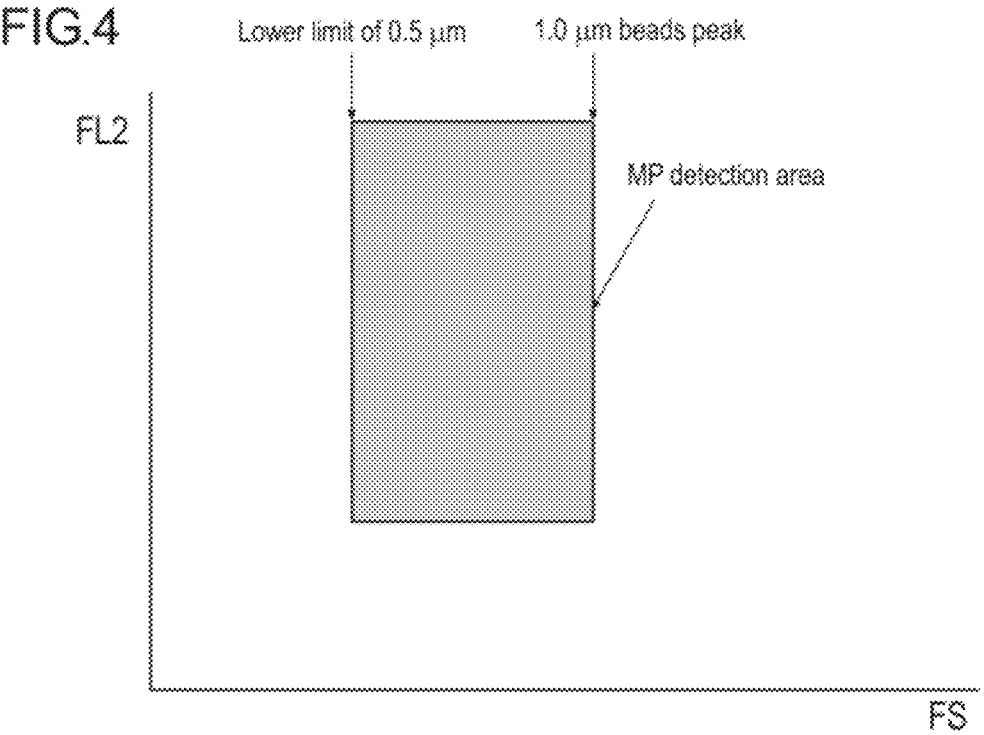
FIG. 4 is an illustrative diagram for explaining a step where a TF detection area on FS×FL cytogram is determined.

On the other hand, after preparing the FS×FL cytogram, as shown in FIG. 4, TF detection area (gate) is determined. On this occasion, the lower limit position on vertical axis (FL) may be set so that the non-specifically stained particles can be eliminated as much as possible from the area.

Figure 5:
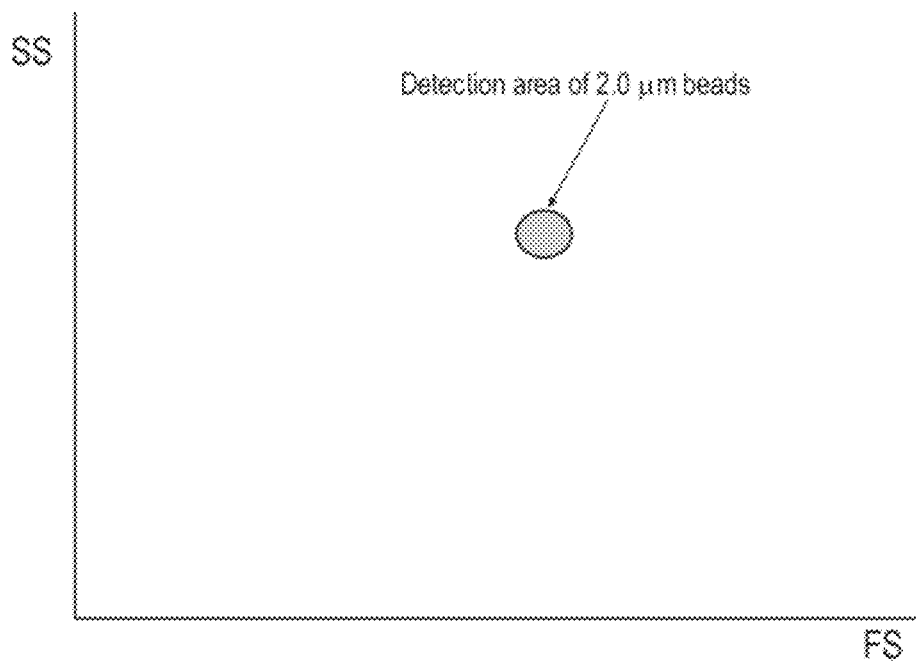
FIG. 5 is an illustrative diagram for explaining a step where an upper limit position of particle size of the EDMP detection area in FS of FS×SS cytogram is determined by measuring setting beads which have a mean particle size of 2.0 μm.

On the other hand, with respect to EDMP, according to the study conducted by the present inventors, since the results of emerging events of larger than 1.5 μm were also observed, the upper limit of FS was decided to be extended so as to include the majority of those events. In this regard, however, since it is necessary to eliminate background noise and big vesicles which are apoptotic bodies containing nuclear material as much as possible, the upper limit of FS was decided to be extended to 2.0 μm. Consequently, here, as shown in FIG. 5, the setting beads having a mean particle size of 2.0 μm are measured, and by a peak value of the aforementioned setting beads, upper limit position of the particle size of EDMP detection area in FS is determined.

Figure 6:
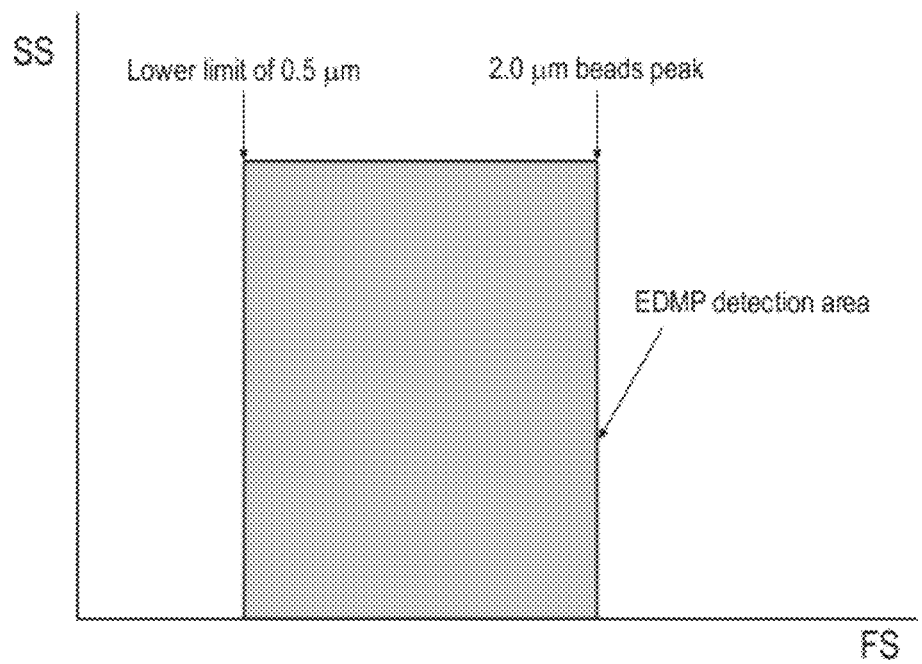
FIG. 6 is an illustrative diagram for explaining a step where a primary area (primary gate) for EDMP detection on FS×SS cytogram is determined.
Figure 7:
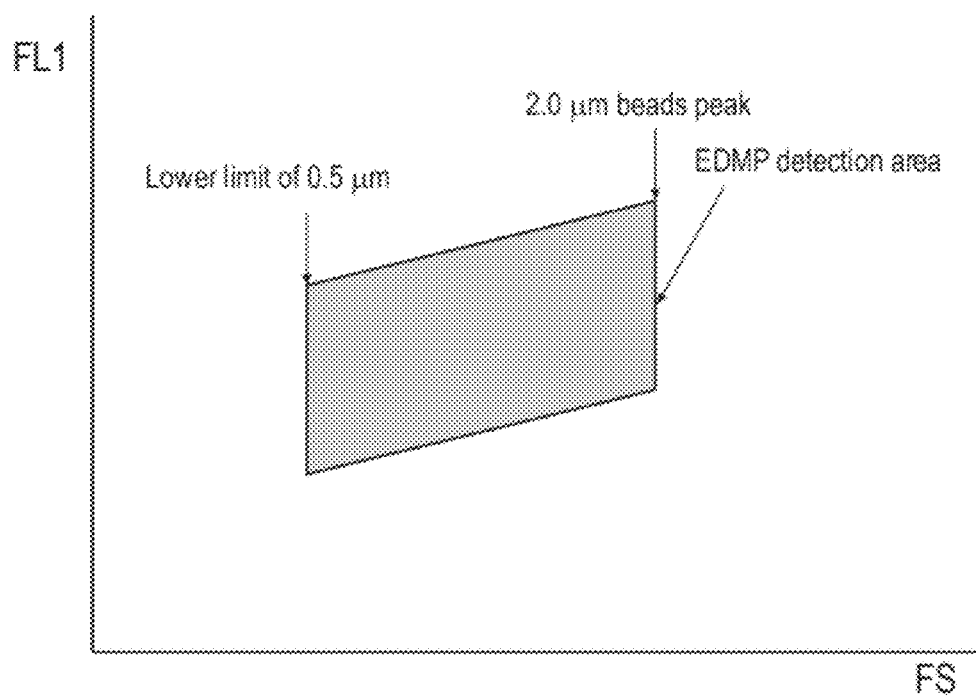
FIG. 7 is an illustrative diagram for explaining a step where an EDMP detection area on FS×FL cytogram is determined.

After that, as the same way mentioned above, on the FS×SS cytogram, as shown in FIG. 6, primary area (primary gate) for EDMP detection is determined, and on the FS×FL cytogram, as shown in FIG. 7, EDMP detection area (gate) is determined.

Subsequently, measurement is carried out for the measurement sample prepared above, and EDMP and TF are detected and determined quantitatively. In addition, the same detection and quantitative determination are carried out for the sample using isotype control of each antibody, and thereby, nonspecific staining is checked to be minimum.

After that, the positive area in each FS-FL scattergram of EDMP and TF is subjected to the secondary gating, and events included in the gate are used as MP event. As to the obtained MP event, by re-developing on the FS-SS scattergram, information on the size of the MP event can also be obtained (see, FIG. 9A and FIG. 9B)

Figure 10:
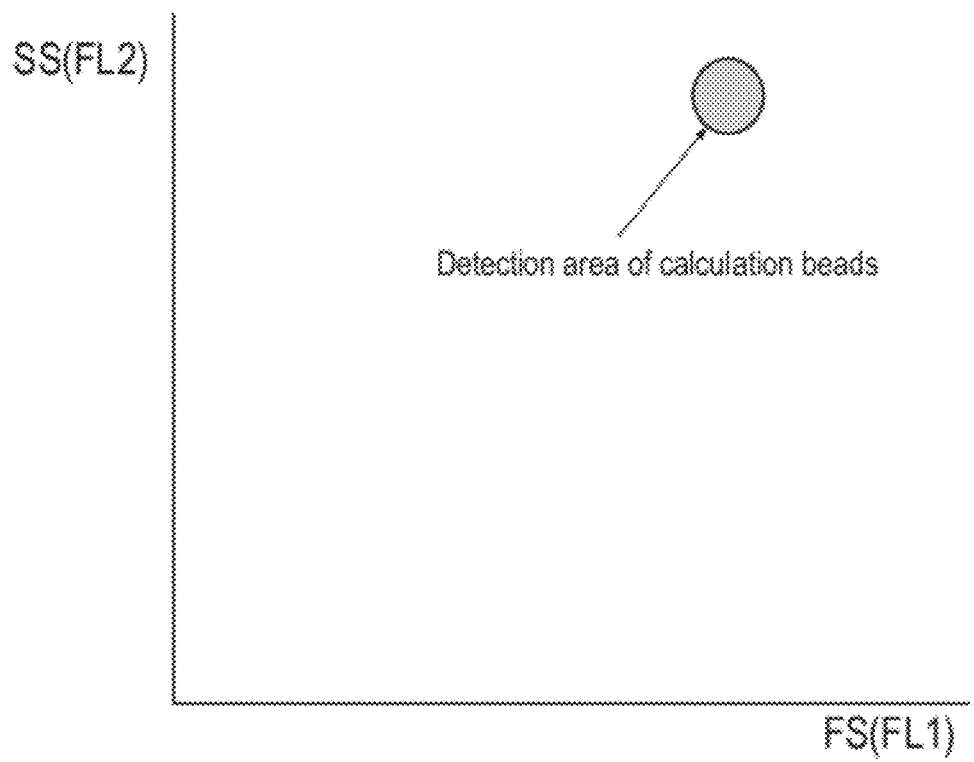
FIG. 10 is an illustrative diagram for explaining a step where beads for calculation are measured.

Finally, as shown in FIG. 10, by counting the number of beads for calculation, concentration (number/µL of plasma) of detected EDMP and TF are calculated.

As mentioned above, although the method of the present invention was explained in detail by taking the case where the MP in a blood sample is detected and determined quantitatively by the flow cytometry method as an example, in some situations, the MP in a blood sample may be detected and determined quantitatively by other techniques. Besides the flow cytometry method, the technique that can be used for the detection and quantitative determination includes, for example, the filtration method, the enzyme-linked immunosorbent assay (ELISA) method and so on.

According to further another aspect of the present invention, there is provided a testing kit of vascular endothelial damage. Said testing kit comprises:

an antibody which specifically recognizes vascular endothelial cell-derived microparticle; and an antibody which specifically recognizes tissue factor-containing microparticle; as essential components. Since specific embodiments of these two kinds of antibodies are as mentioned above, detailed description is omitted here.

In addition, in the above-described testing kit, the first and the second antibodies are preferably labeled with fluorescent dye (for example, fluorescein isothiocyanate, phycoerythrin-Cy5, phycoerythrin, or the like), and in this case, said testing kit may be used for testing with the flow cytometry method as mentioned above. Furthermore, in this case, the testing kit preferably further comprises:

setting beads for defining upper limit position of particle size within the detection area of the vascular endothelial cell-derived microparticle (EDMP);

setting beads for defining upper limit position of particle size within the detection area of the tissue factor-containing microparticle (TF);

beads for calculation of known concentration; and threshold beads for defining minimum intensity threshold value within the detection area of microparticle. In addition, a mean particle size of the threshold beads is preferably 0.5 µm; a mean particle size of the beads for calculation is preferably 3 to 5 µm; and mean particle sizes of the first and the second setting beads should be preferably 1 and 2 µm.

The testing kit to be provided by the present invention may be the one which comprises, besides the components mentioned above, for example, buffer solution for diluting sample and reagent, reaction vessel, positive control, negative control, and written directive indicating test protocol, and the like. These elements can also be mixed in advance if necessary. By using this kit, the test of the present invention for vascular endothelial damage and for risk factor related to the prevention and development of metabolic syndrome become simple, and it is very useful for early diagnosis and/or decision on the course of treatment.

EXAMPLES

Hereinafter, the present invention will be explained in detail by referring to the following Examples, however, the present invention is by no means limited only to the following Examples.

Preparation of the Sample for Measurement

Peripheral blood was collected from patients who have defective heart valves, patients who have received percutaneous coronary intervention (PCI) for ischemic heart disease, or patients who received catheterization as a high risk group of vascular endothelial damage (total 20 patients), and after making sure that CRP value is less than 0.2 mg/dL, it was used for the following experiment. On this occasion, EDTA was used as an anticoagulant at the time of collection of the blood. On the other hand, as a sample of healthy subject, the peripheral blood which was collected from healthy volunteer (healthy men and women of 24 to 47 years old, 29 persons) using citrate blood collection tube was used. In addition, written informed consent was obtained from all of the patients and healthy volunteers.

The collected blood was transferred to a micro tube made of PP (produced by Assist A. 150), and was centrifuged to separate plasma component. The obtained platelet poor plasma (PPP) was transferred to another micro tube made of PP and used as a sample for measurement. In addition, centrifugation condition of the plasma separation was at 8000 g for 5 minutes. And also, the obtained PPP was kept at 4° C. and used on the same day. When the measurement could not be performed on the same day, the plasma was preserved in a frozen state below −20° C. until measured, and measurement was performed immediately after thawing.

Example 1

Measurement Examples of EDMP and TF

In the case where measurement was carried out using a sample derived from patient group, at first, 2.5 µL each of FITC labeled anti-CD144 polyclonal antibodies (produced by Serotec, Oxford UK) which specifically recognizes VE-cadherin and PE labeled anti-CD142 antibody (produced by BD Biosciences)which specifically recognizes TF were added to the TruCount™ tube (produced by BD Biosciences), and further 50 µL of the sample for measurement prepared above was added. It should be noted that TruCount™ beads used for absolute counting were contained in lyophilized state in the TruCount™ tube. On the other hand, in the case that measurement was carried out using a sample derived from healthy subject, instead of using TruCount™ tube, the beads for calculation of known concentration (polystyrene beads having a mean particle size of 3.0 µm, $1.68 \times 10^9$ particles/mL (produced by Polyscience, Philadelphia USA)) were diluted and dispensed by 50000 particles. In addition, from the estimated value of the MP level in the plasma, it was confirmed that the addition amount of antibodies was sufficient.

The antibody was reacted with MP in the plasma by incubating at room temperature for 15 minutes under light shading, then diluted by adding 450 µL of PBS (containing 0.1% BSA) to prepare a measurement sample.

In addition, prior to measurement using the above samples, TF detection area and EDMP detection area were determined by the following procedures. Further, BD FACSCanto™ II Flow Cytometer (produced by BD Biosciences) was employed in the flow cytometry method.

First, a FS×SS cytogram was prepared. Subsequently, as shown in FIG. 1, the threshold beads having a mean particle size of 0.5 μm was measured, and the lower limit position of particle size of MP detection area in FS was determined.

Figure 3:
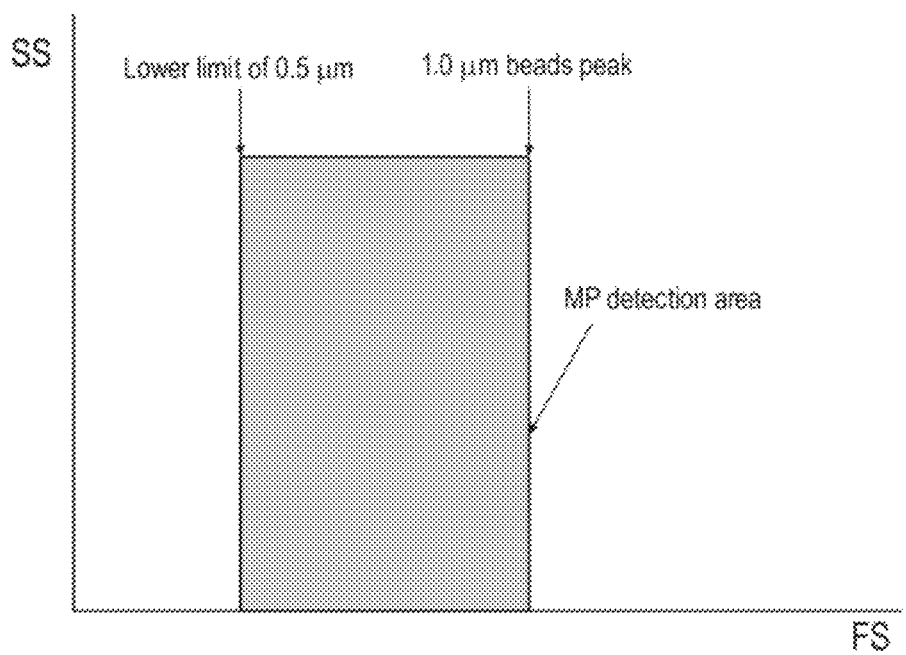
FIG. 3 is an illustrative diagram for explaining a step where a primary area (primary gate) for TF detection on FS×SS cytogram is determined.

Subsequently, as shown in FIG. 2, the setting beads having a mean particle size of 1.0 μm were measured, and the upper limit position of particle size of TF detection area in FS was determined. Furthermore, on the FS×SS cytogram, as shown in FIG. 3, the primary area (primary gate) for TF detection was determined. Thus, FS×FL2 cytogram was prepared, and as shown in FIG. 4, TF detection area was determined.

On the other hand, as shown in FIG. 5, the setting beads having a mean particle size of 2.0 μm were measured, and the upper limit position of particle size of EDMP detection area in FS was determined. Furthermore, on the FS×SS cytogram, by the same way as shown in FIG. 6, the primary area (primary gate) for EDMP detection was determined. Also, FS×FL1 cytogram was prepared, as shown in FIG. 7, EDMP detection area was determined.

Figure 8:
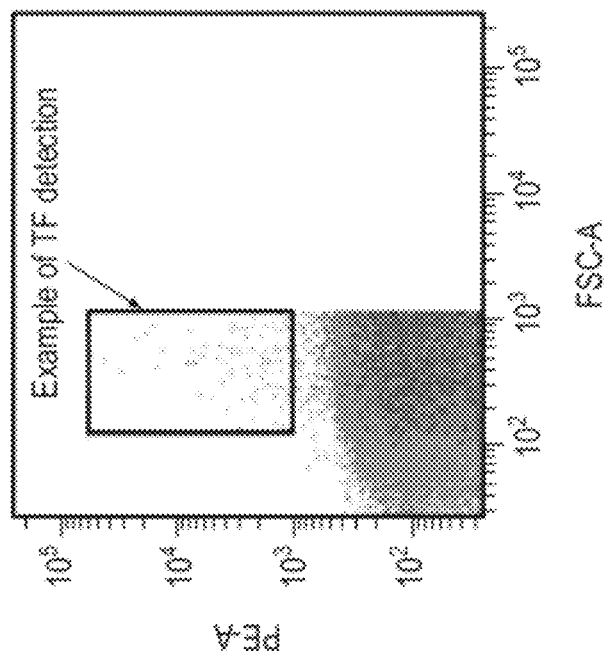
FIG. 8 is a diagram showing the results of detection of EDMP and TF in a measurement sample in Example 1.
Figure 8:
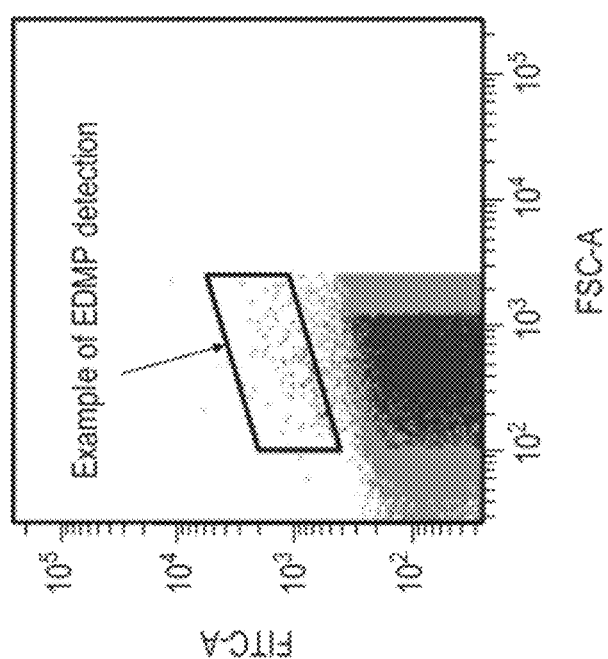
Figure 9A:
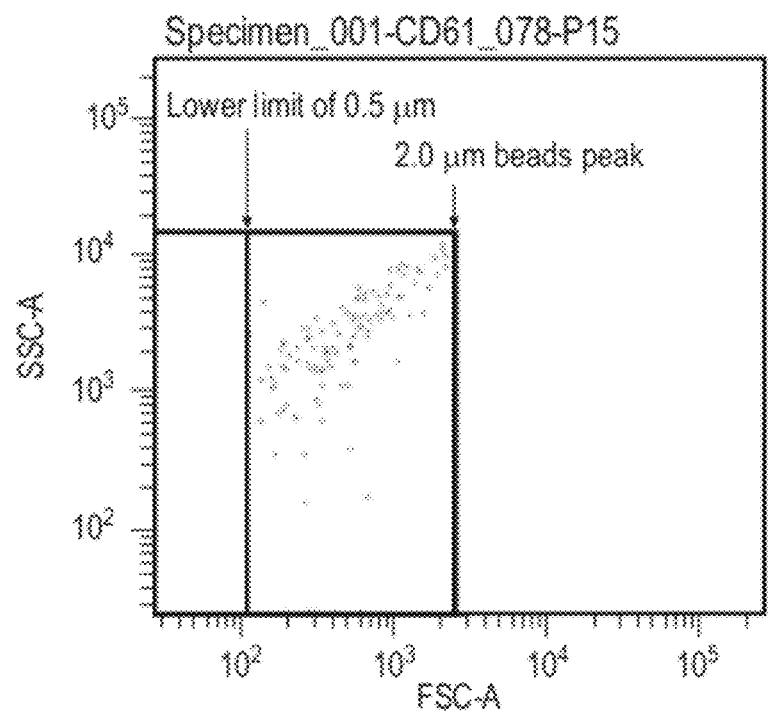
FIG. 9A is a diagram showing the results of re-developed EDMP detection results on FS×SS scattergram in Example 1.
Figure 9B:
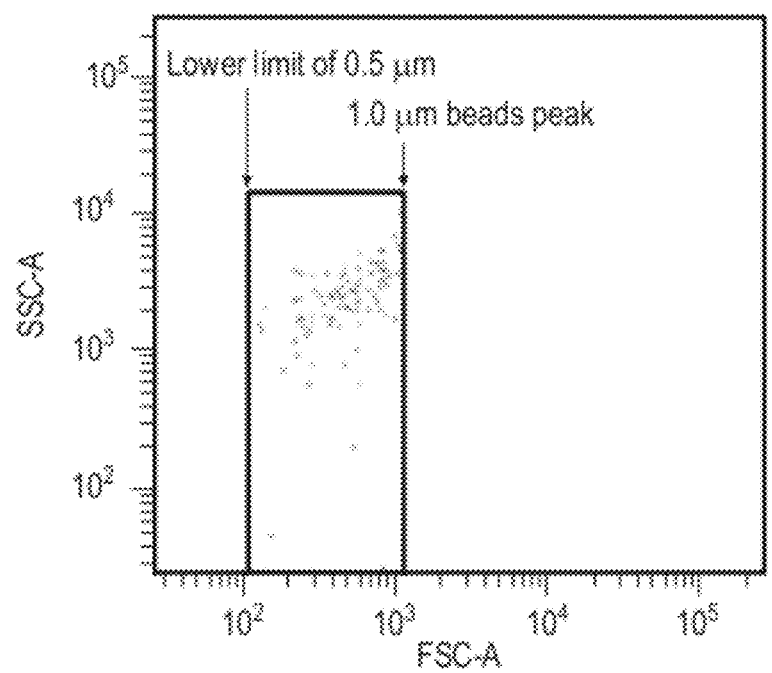
FIG. 9B is a diagram showing the results of re-developed TF detection results on FS×SS scattergram in Example 1.

Subsequently, measurement was carried out for the measurement sample prepared above, and EDMP and TF in the measurement sample were detected. In addition, the same measurement was carried out for the sample using isotype control of each antibody (or serum), and thereby, nonspecific staining was checked. FIG. 8 shows the respective detection results. In addition, FIG. 9A shows an aspect of re-developed EDMP detection result on FS×SS scattergram; and FIG. 9B shows an aspect of re-developed TF detection result on FS×SS scattergram.

Finally, as shown in FIG. 10, the TruCount™ beads or polystyrene beads used as a beads for calculation were measured, and based on the value, concentrations of detected EDMP and TF in the plasma (particles/μL plasma) were calculated.

Figure 11A:
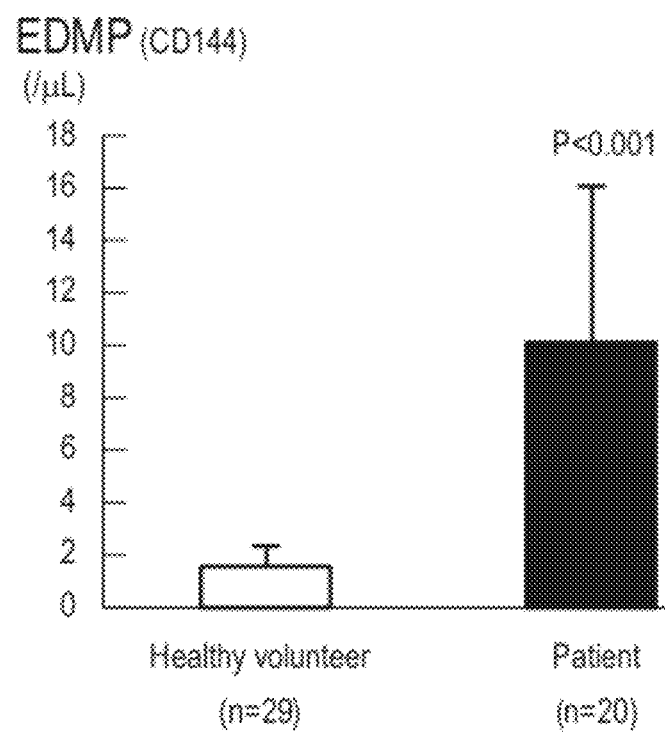
FIG. 11A is a graph showing a comparison between EDMP concentration (mean value±standard deviation) in a measurement sample derived from healthy volunteers and EDMP concentration (mean value±standard deviation) in a measurement sample derived from patients, which were measured in Example 1.
Figure 11B:
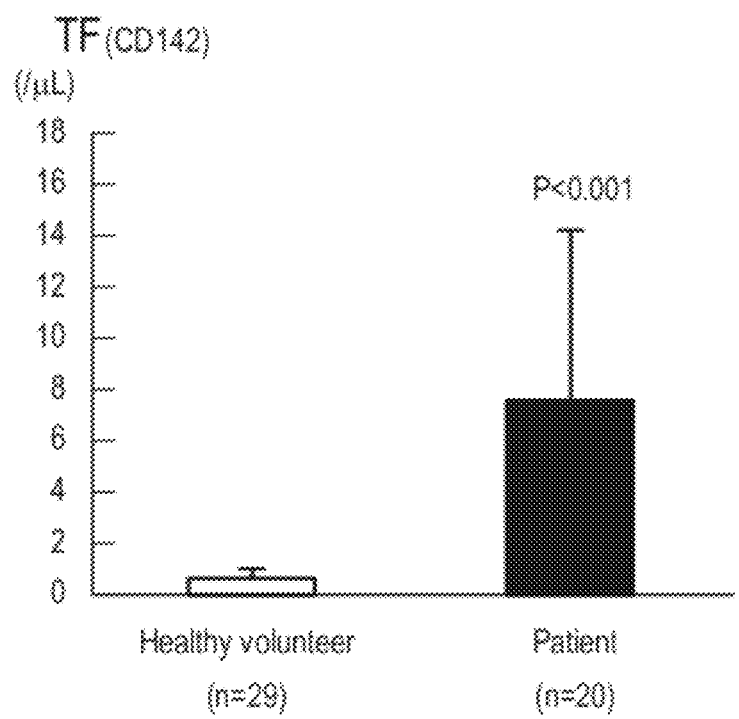
FIG. 11B is a graph showing a comparison between TF concentration (mean value±standard deviation) in a measurement sample derived from healthy volunteers and TF concentration (mean value±standard deviation) in a measurement sample derived from patients, which were measured in Example 1.

Correlation coefficient r between EDMP concentration and TF concentration in the measurement sample derived from patient obtained as mentioned above was calculated, and very high correlation coefficient as r=0.87 was observed. Here, as shown in FIG. 11A (EDMP concentration) and FIG. 11B (TF concentration), both of EDMP concentration (mean value) and TF concentration (mean value) in the measurement sample derived from healthy volunteer showed values significantly smaller than the value (mean value) in the measurement sample derived from patient. From this finding, it was suggested that by using EDMP concentration and TF concentration in the plasma in combination as a marker of pathological condition of vascular endothelial damage, detection and evaluation of vascular endothelial damage could be performed with a high degree of accuracy. It should be noted that each value shown in the graph of FIG. 11A and FIG. 11B is mean value±standard deviation in each measurement sample derived from patient and healthy volunteer.

Example 2

Measurement Example of EDMP, TF and PDMP

In the case where measurement was carried out using a sample derived from patient group, at first, 2.5 μL each of FITC labeled anti-CD144 polyclonal antibodies which specifically recognize VE-cadherin included in EDMP (produced by Serotec, Oxford UK) and PE labeled anti-CD142 antibody which specifically recognizes TF (produced by BD Biosciences), and PerCP-Cy5.5 labeled anti-CD41 antibody which specifically recognizes PDMP (produced by DAKO, Glostrup Denmark) were added to the TruCount™ tube (produced by BD Biosciences), and further 50 μL of the sample for measurement which was prepared above was added. In addition, TruCount™ beads which were beads for calculation were contained in lyophilized state in the TruCount™ tube. On the other hand, in the case where measurement was carried out using a sample derived from healthy subject, instead of using TruCount™ tube, the beads for calculation of known concentration (polystyrene beads having a mean particle size of 3.0 μm, $1.68 \times 10^9$ particles/mL (produced by Polyscience, Philadelphia USA)) was diluted and dispensed by 50000 particles. In addition, from the estimated value of the MP level in the plasma, it was confirmed that the addition amount of antibodies was sufficient.

The antibody was reacted with MP in the plasma by incubating at room temperature for 15 minutes under light shading, then diluted by adding 450 μL of PBS (containing 0.1% BSA) to prepare a measurement sample.

In addition, prior to measurement using the measurement sample, TF detection area, PDMP detection area, and EDMP detection area were determined by the following procedures. In addition, BD FACSCanto™ II Flow Cytometer (produced by BD Biosciences) was employed in the flow cytometry method.

First, a FS×SS cytogram was prepared. Subsequently, as shown in FIG. 1, the threshold beads having a mean particle size of 0.5 μm were measured, and the lower limit position of particle size of MP detection area in FS was determined.

Figure 12:
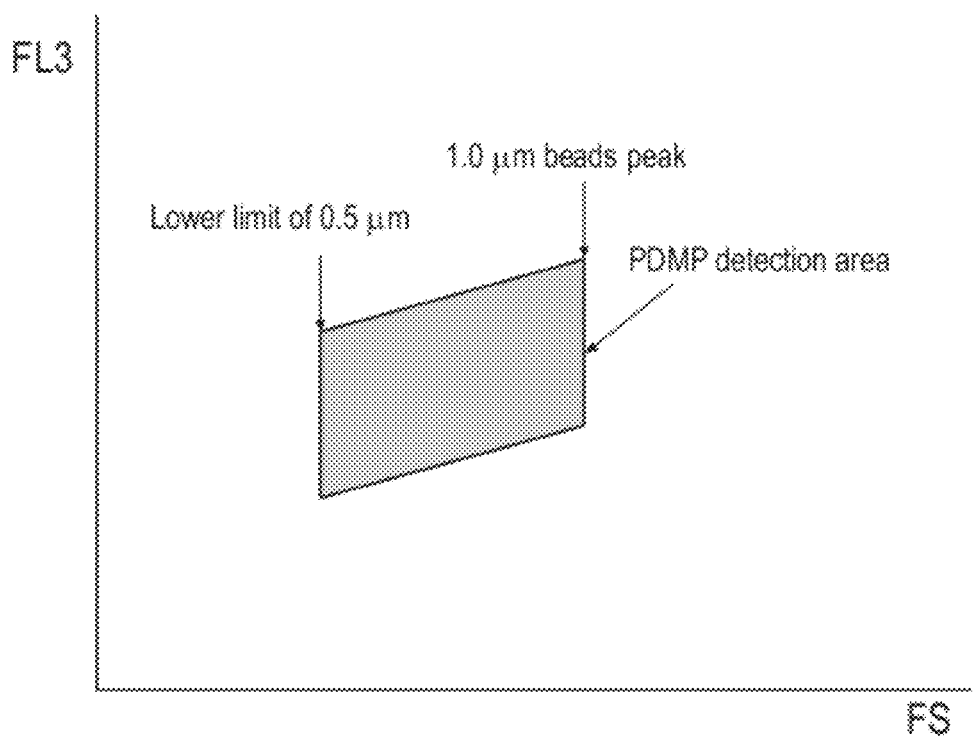
FIG. 12 is an illustrative diagram for explaining a step where a PDMP detection area on FS×FL cytogram is determined.

Subsequently, as shown in FIG. 2, the setting beads having a mean particle size of 1.0 μm were measured, and the upper limit position of particle size of TF detection area and PDMP detection area in FS were determined. Furthermore, on the FS×SS cytogram, as shown in FIG. 3, the primary areas (primary gates) for the detection of TF and PDMP were determined. Also, FS×FL2 cytogram was prepared, and as shown in FIG. 4, TF detection area was determined. And also, FS×FL3 cytogram was prepared, and as shown in FIG. 12, PDMP detection area was determined.

On the other hand, as shown in FIG. 5, the setting beads having a mean particle size of 2.0 μm was measured, and the upper limit position of particle size of EDMP detection area in FS was determined. Furthermore, on the FS×SS cytogram, as shown in FIG. 6, the primary area (primary gate) for EDMP detection was determined. Also, FS×FL1 cytogram was prepared, and shown in FIG. 7, EDMP detection area was determined.

Figure 13:
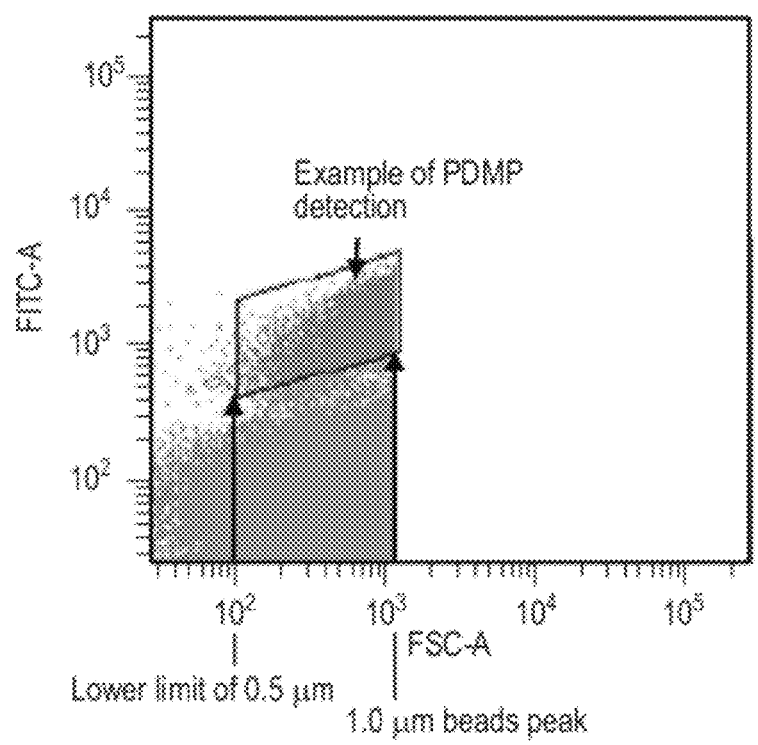
FIG. 13 is a diagram showing the results of PDMP detection in a measurement sample in Example 2.
Figure 14:
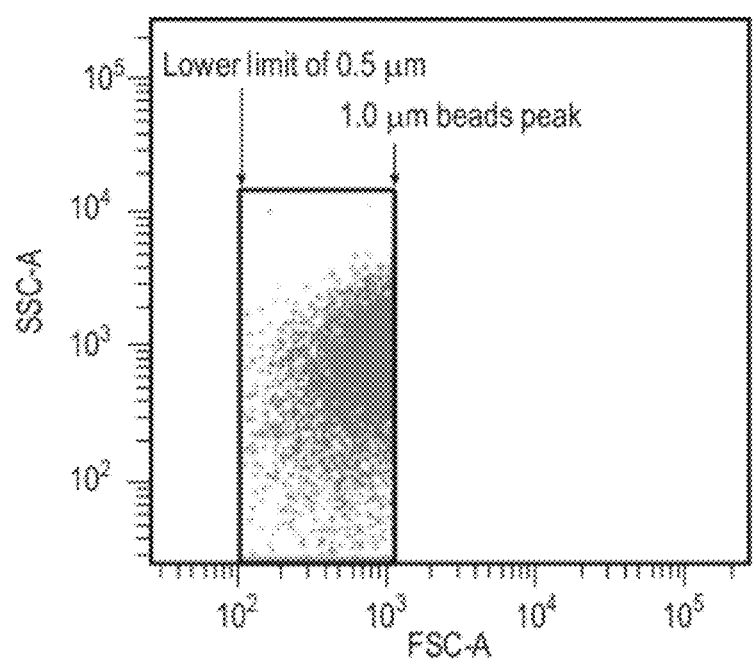
FIG. 14 is a diagram showing the results of re-developed PDMP detection results on FS×SS scattergram in Example 2.

Subsequently, measurement was carried out for the sample prepared above, and EDMP, TF, and PDMP in the measurement sample were detected. In addition, same measurement was carried out for the sample using isotype control for the each specific antibody, and thereby, nonspecific staining was checked. FIG. 13 shows the results of PDMP detection. In addition, FIG. 14 shows an aspect of re-developed PDMP detection results on FS×SS scattergram.

Figure 15:
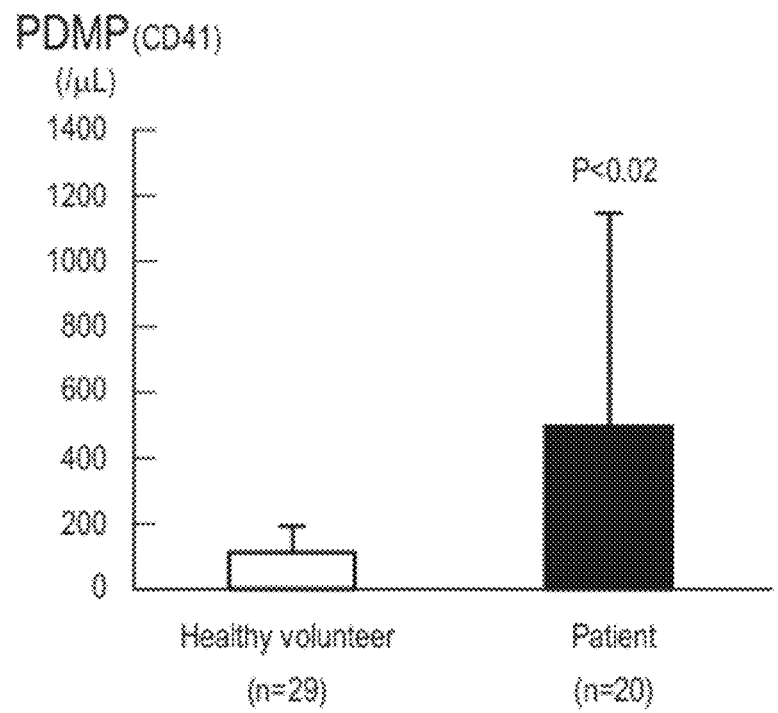
FIG. 15 is a graph showing a comparison between PDMP concentration (mean value±standard deviation) in a measurement sample derived from healthy volunteers and PDMP concentration (mean value±standard deviation) in a measurement sample derived from patients, which were measured in Example 2.

Finally, as shown in FIG. 10, the TruCount™ beads or polystyrene beads used as a beads for calculation were measured, and based on the value, concentrations of detected EDMP, TF, and PDMP in the plasma (particles/μL plasma) were calculated. Here, similarly to Example 1 described above, the PDMP concentration (mean value) in the measurement sample derived from healthy volunteer showed a value significantly smaller than the value (mean value) in the measurement sample derived from patient. In addition, as shown in FIG. 15, the PDMP concentration (mean value) in the measurement sample derived from healthy volunteer showed the value significantly smaller than the value (mean value) in the measurement sample derived from patient. From this finding, it was suggested that in addition to EDMP concentration and TF concentration which were discussed in Example 1, by further using PDMP concentration in combination as a marker of pathological condition of vascular endothelial damage, detection and evaluation of vascular endothelial damage could be performed in more high degree of accuracy. It should be noted that each value shown in the graph of FIG. 15 is mean value±standard deviation in each measurement sample derived from healthy volunteer and patient.

Example 3

Measurement Example of EDMP, TF, PDMP, and MDMP

In the case where measurement was carried out using a sample derived from patient group, at first, 2.5 µL each of FITC labeled anti-CD144 antibod (produced by Serotec, Oxford UK) which specifically recognizes VE-cadherin included in EDMP, PE labeled anti-CD142 antibody which specifically recognizes TF (produced by BD Biosciences), PerCP-Cy5.5 labeled anti-CD41 antibody which specifically recognizes PDMP (produced by DAKO, Glostrup Denmark), and PE-Cy7 labeled CD11b antibody which specifically recognizes MDMP were added to the TruCount™ tube (produced by BD Biosciences), and further 50 µL of the sample for measurement which was prepared above was added. In addition, TruCount™ beads which were beads for calculation were contained in lyophilized state in the TruCount™ tube. On the other hand, in the case where measurement was carried out using a sample collected from healthy subject, instead of using TruCount™ tube, the beads for calculation of known concentration (polystyrene beads having a mean particle size of 3.0 µm, $1.68 \times 10^9$ particles/mL (produced by Polyscience, Philadelphia USA)) were diluted and dispensed by 50000 particles. In addition, from the estimated value of the MP level in the plasma, it was confirmed that the addition amount of antibodies was sufficient.

The antibody was reacted with MP in the plasma by incubating at room temperature for 15 minutes under light shading, then diluted by adding 450 µL of PBS (containing 0.1% BSA) to prepare a measurement sample.

In addition, prior to measurement using the sample, TF detection area, PDMP detection area, and EDMP detection area were determined by the following procedures. In addition, BD FACSCanto™ II Flow Cytometer (produced by BD Biosciences) was employed in the flow cytometry method.

First, a FS×SS cytogram was prepared. Subsequently, as shown in FIG. 1, the threshold beads having a mean particle size of 0.5 µm were measured, and the lower limit position of particle size of MP detection area in FS was determined.

Figure 16:
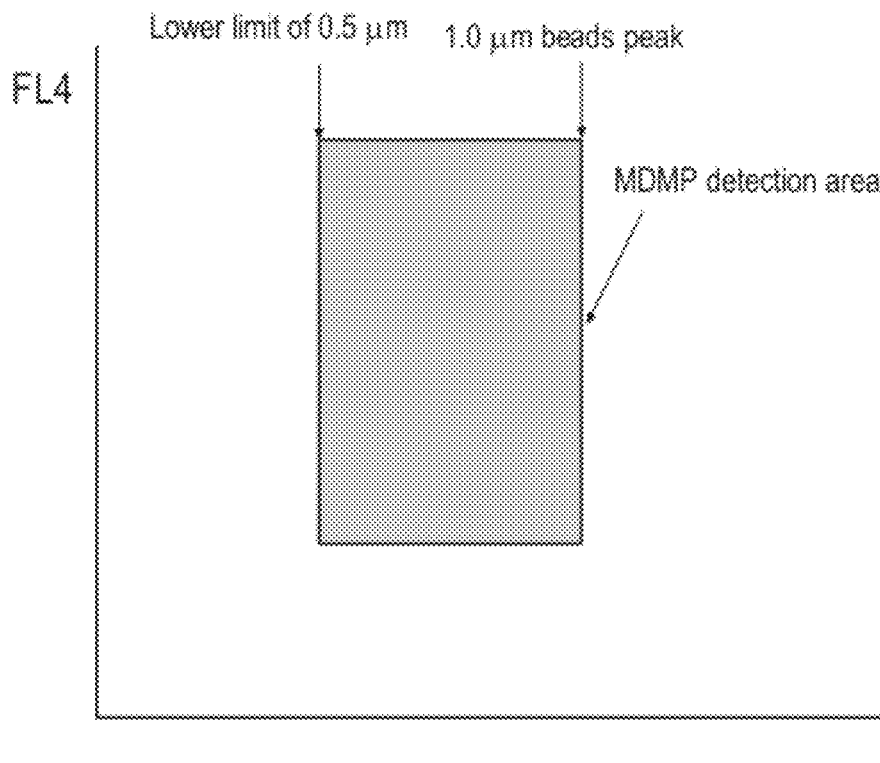
FIG. 16 is an illustrative diagram for explaining a step where a MDMP detection area on FS×FL cytogram is determined.

Subsequently, as shown in FIG. 2, the setting beads having a mean particle size of 1.0 µm were measured, and the upper limit position of particle size of TF detection area, PDMP detection area, and MDMP detection area in FS were determined. Furthermore, on the FS×SS cytogram, as shown in FIG. 3, the primary areas (primary gates) for the detection of TF, PDMP, and MDMP were determined. In addition, FS×FL2 cytogram was prepared, and as shown in FIG. 4, TF detection area was determined. And also, FS×FL3 cytogram was prepared, and as shown in FIG. 12, PDMP detection area was determined. Further, FS×FL4 cytogram was prepared, and as shown in FIG. 16, MDMP detection area was determined.

On the other hand, as shown in FIG. 5, the setting beads having a mean particle size of 2.0 µm were measured, and the upper limit position of particle size of EDMP detection area in FS was determined. Furthermore, on the FS×SS cytogram, as shown in FIG. 6, the primary area (primary gate) for EDMP detection was determined. Also, FS×FL1 cytogram was prepared, and as shown in FIG. 7, EDMP detection area was determined.

Figure 17:
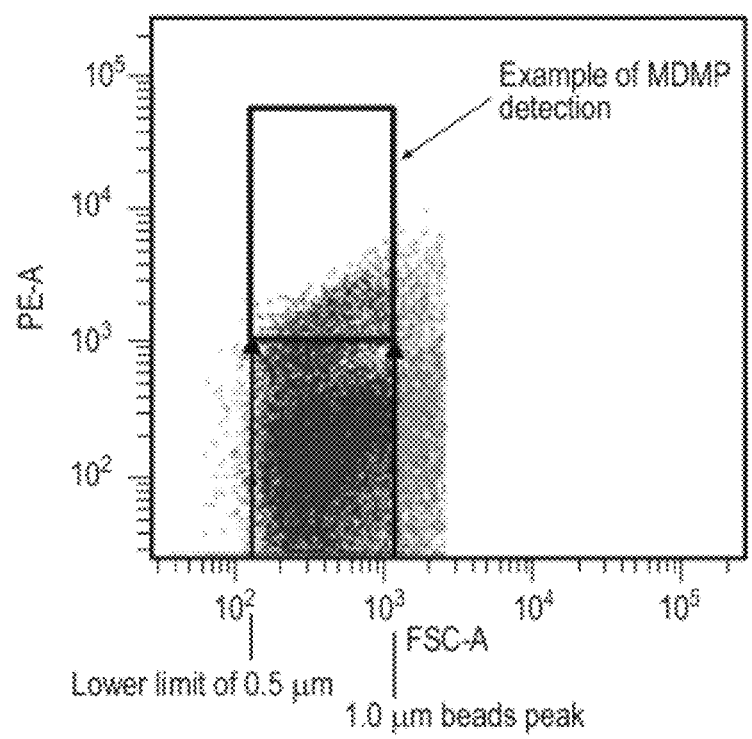
FIG. 17 is a diagram showing the results of MDMP detection in a measurement sample in Example 3.
Figure 18:
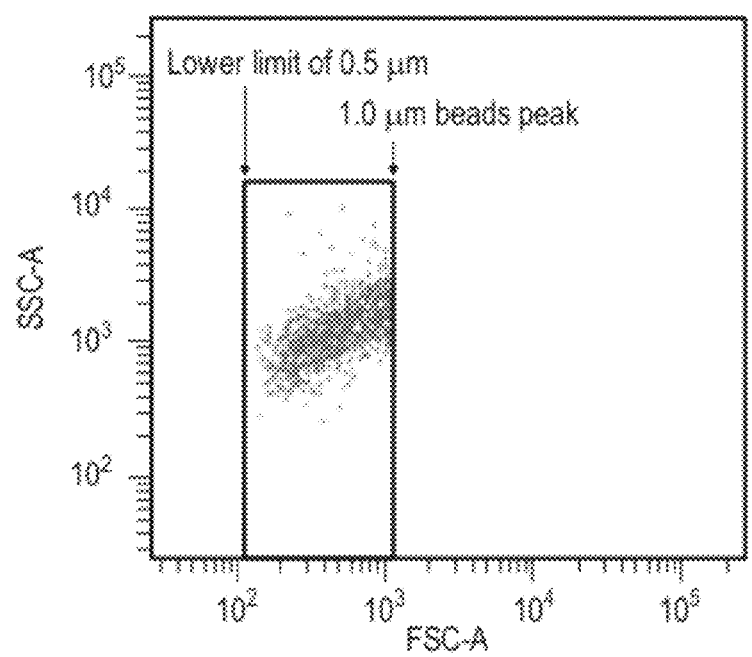
FIG. 18 is a diagram showing the results of re-developed MDMP detection result on FS×SS scattergram in Example 3.

Subsequently, measurement was carried out for the measurement sample prepared above, and EDMP, TF, PDMP, and MDMP in the measurement sample were detected. In addition, the same measurement was carried out for the sample using isotype control of each antibody, and thereby, nonspecific staining was checked. FIG. 17 shows the results of MDMP detection. In addition, FIG. 18 shows an aspect of re-developed MDMP detection result on FS×SS scattergram.

Finally, as shown in FIG. 10, the TruCount™ beads or polystyrene beads used as a beads for calculation were measured, and based on the value, concentrations of detected EDMP, TF, PDMP, and MDMP in the plasma (particles/µL plasma) were calculated.

It should be noted that the present application was based on Japanese Patent Application Number 2011-029027 filed on Feb. 14, 2011, and the disclosure is incorporated by reference in its entirety.

What is claimed is:

1. A method for diagnosing vascular endothelial damage in a patient, said method comprising the steps of:
   obtaining a whole blood sample from the patient;
   separating a platelet poor plasma sample from the blood sample by gently removing the blood cells from the blood sample so as to reduce contamination by blood cell microparticles; and
   simultaneously quantitatively measuring the amount of vascular endothelial cell-derived microparticles (EDMP) in said plasma sample and quantitatively measuring the amount of tissue factor-containing microparticles (TF) in said plasma sample;
   wherein the extent of vascular endothelial damage in said patient is diagnosed based on the amounts of vascular endothelial cell-derived microparticles and tissue factor-containing microparticles measured in said plasma sample that are in excess of the amounts measured in significant healthy patients without vascular endothelial damage.

2. The method according to claim 1, wherein:
   the simultaneous quantitative measuring step is carried out using a first antibody which recognizes specifically the vascular endothelium-derived microparticle; and a second antibody which recognizes specifically the tissue factor-containing microparticle.

3. The method according to claim 2, wherein said first antibody is an anti-CD144 polyclonal antibody and said second antibody is an anti-CD142 antibody.

4. The method according to claim 2, wherein said first antibody and said second antibody are each labeled with different fluorescent dyes, and said simultaneous quantitative measuring step is carried out using a flow cytometry method.

5. The method of claim 2, further comprising the step of estimating the maximum microparticle concentration of the plasma sample before the microparticle measurement step, wherein said estimated maximum microparticle concentration of said plasma sample is used to determine sufficient amounts of said first and second antibodies.

6. The method according to claim 1, further comprising the step of:
   quantitatively measuring platelet-derived microparticles (PDMP) in said plasma sample.

7. The method according to claim 1, further comprising the step of:

quantitatively measuring monocyte-derived microparticles (MDMP) in said plasma sample.

8. The method according to claim 1, further comprising the step of:
quantitatively measuring neutrophil-derived microparticles (NDNP) in said plasma sample.

9. A method for determining microparticle concentrations in a mammalian patient blood sample that are relevant to diagnosing vascular endothelial damage, said method comprising the steps of:
obtaining a whole blood sample from the patient;
separating a platelet poor plasma sample from said blood sample by gently removing the blood cells from said blood sample so as to reduce contamination by blood cell microparticles;
estimating the maximum microparticle concentration of said plasma sample; and
simultaneously quantitatively measuring the amount of vascular endothelial cell-derived microparticles (EDMP) in said plasma sample using an amount of a first antibody quantitatively measuring; and quantitatively measuring the amount of tissue factor-containing microparticles (TF) in said plasma sample, using an amount of a second antibody which specifically recognizes TF;
wherein said estimated maximum microparticle concentration of said plasma sample is used to used in simultaneously measuring the amount of vascular endothelial cell-derived microparticles and the amount of tissue factor-containing microparticles in the plasma sample.

* * * * *